United States Patent [19]

Meyer

[11] Patent Number: 4,893,495

[45] Date of Patent: Jan. 16, 1990

[54] OXYGEN SENSING METHOD AND APPARATUS

[75] Inventor: Emilio Meyer, Assago-Milan, Italy

[73] Assignee: Panametrics, Inc., Waltham, Mass.

[21] Appl. No.: 252,812

[22] Filed: Oct. 3, 1988

[51] Int. Cl.$^4$ ............................................. G01N 27/74
[52] U.S. Cl. ..................................................... 73/27 A
[58] Field of Search ........................ 73/27 A; 324/204

[56] References Cited

U.S. PATENT DOCUMENTS

| | | | |
|---|---|---|---|
| 2,693,103 | 11/1954 | Krupp | 73/27 A |
| 2,944,418 | 7/1960 | Englehardt | 73/27 A |
| 2,951,359 | 9/1960 | Krupp | 73/27 A X |
| 3,064,465 | 11/1962 | Richardson | 73/27 A |
| 3,276,244 | 10/1966 | Wilson et al. | 73/27 A |
| 3,292,421 | 12/1966 | Meyer | 73/27 A |
| 3,435,662 | 4/1969 | Meyer | 73/27 A |
| 3,616,679 | 11/1971 | Meyer et al. | 73/27 A |
| 3,646,803 | 3/1972 | Meyer | 73/27 A |

FOREIGN PATENT DOCUMENTS 64957 10/1946 Denmark ............................ 73/27 A Primary Examiner—John Chapman
Assistant Examiner—Joseph W. Roskos
Attorney, Agent, or Firm—Lahive & Cockfield

[57] ABSTRACT

Oxygen sensing apparatus and methods utilize a sensing cell including two pairs of electrically heated thermistors and a source of an inhomogeneous magnetic field. One thermistor of each pair is positioned inside the magnetic field, and the second thermistor of each pair is positioned adjacent to the respective first thermistor of each pair, substantially outside the magnetic field. When oxygen is present in the sensing cell, the thermistors inside the magnetic field generate a gas flow in the direction of the adjacent thermistors of each pair positioned outside the magnetic field, thus tending to reduce the temperature of the thermistors inside the field and increase the temperature of the thermistors outside the field. The thermistors are connected in a measuring bridge circuit including elements for maintaining the temperature of the thermistors at a substantially constant level, thereby providing a signal that can be used to compensate for changes in the thermal characteristics of the background gases.

8 Claims, 1 Drawing Sheet

W1, W2 = WIND GENERATING THERMISTORS
R1, R2 = WIND SENSING THERMISTORS

OXYGEN SENSING METHOD AND APPARATUS

BACKGROUND OF THE INVENTION

This invention relates generally to oxygen sensing methods and apparatus, and, more particularly, relates to apparatus and methods for measuring oxygen concentration in gas mixtures by magnetic means.

Accurate measurement of oxygen concentration in a gas mixtures is important in a wide range of industrial, clinical and laboratory processes. A wide range of devices have therefore been proposed or developed for measuring oxygen concentration. It has long been recognized that oxygen is paramagnetic, in that its molecules seek the strongest part of a magnetic field. Most other gases, in contrast, are diamagnetic, in that their molecules seek the weakest part of a magnetic field. The widely recognized paramagnetic properties of oxygen have stimulated a number of investigations into methods and apparatus for measuring oxygen concentration in gas mixture by magnetic sensing apparatus.

An early type of paramagnetic measuring cell, which relied upon the magnetic susceptibility of oxygen, is described in Pauling, et al, "An Instrument for Determining the Partial Pressure of Oxygen in a Gas", 68 *Journal of the American Chemical Society* 795, (1946). The Pauling et al measuring cell utilizes a sealed glass tube containing a weakly diamagnetic gas, such as nitrogen. The tube is suspended between the wedge-shaped pole pieces of a permanent magnet, which provide a non-uniform magnetic field, and the tube is free to rotate about a vertical axis. The entire structure is then placed within a chamber containing a selected gas.

When oxygen is introduced into the chamber surrounding the tube, the nitrogen in the tube is effectively diamagnetic relative to the surrounding paramagnetic oxygen gas, and the tube experiences a force tending to rotate it into the region where the magnetic field is weakest. This movement, or a force required to prevent this movement, can be measured as an indication of the concentration of oxygen in the chamber. The Pauling cell, however, is fragile, and the rotational axis of the tube must be consistently oriented for each use, rendering it unsuitable for industrial oxygen measurement applications.

Another type of apparatus for measuring the concentration of oxygen relies upon the inverse relationship between temperature and the magnetic susceptibility of oxygen. As a result of this inverse relationship, heating a portion of an oxygen-containing mixture in a non-homogeneous magnetic field creates a "magnetic wind" effect, which can be measured through its thermal effect on an electrical resistance element. Various configurations of magnetic wind devices are discussed in Medlock, et al, "Oxygen Analysis", *Transactions of the Instruments and Methods Conference*, Stockholm, 1949, pp. 1–8; and Ellis, et al, "The Measurement of Gaseous Oxygen Tension Utilizing Paramagnetism", 40 *British Journal of Anaesthesia* 569 (1968).

Conventional magnetic wind oxygen measurement devices, however, are subject to relatively large errors due to the changes in the thermal properties of the surrounding, or "background" gases. In particular, the presence of different background gases causes conventional magnetic wind oxygen sensors to yield false readings of oxygen levels, due to the large differences in thermal characteristics of the background gases. Additionally, conventional magnetic wind oxygen sensing devices suffer from position sensitivity and background gas dependency, especially in comparison with methods based on direct measurement of magnetic susceptibility.

Accordingly, there exists a need for oxygen sensing methods and apparatus which provide accurate and reliable measurement of oxygen concentration, regardless of the composition of the background gases.

It is accordingly an object of the invention to provide oxygen sensing methods and apparatus which yield accurate measurement of oxygen concentration, independent of background gas composition and thermal properties.

It is a further object of the invention to provide oxygen measurement apparatus which are rugged, reliable, and readily portable.

Other general and specific objects of the invention will in part be obvious and will in part appear hereinafter.

SUMMARY OF THE INVENTION

The foregoing objects are attained by the invention, which provides apparatus for measuring the concentration of a paramagnetic gas in a gas mixture. In one aspect of the invention, the apparatus includes magnetic field elements for generating an inhomogeneous magnetic field, at least one electrically heated magnetic wind generating thermistor having an electrical parameter proportional to temperature, positioned inside the inhomogeneous magnetic field. The magnetic wind generating thermistor generates a magnetic wind in the presence of a paramagnetic gas, the magnetic wind having a magnitude proportional to concentration of the paramagnetic gas in the gas mixture.

The invention also includes at least one electrically heated magnetic wind sensing thermistor having an electrical parameter proportional to temperature, positioned substantially outside the inhomogeneous magnetic field. The magnetic wind sensing thermistor senses the magnetic wind generated by the magnetic wind generating thermistor in the presence of a paramagnetic gas, by sensing the heat transfer resulting from the magnetic wind.

The invention further includes signal generating elements, in electrical circuit with the magnetic wind generating thermistor elements and the magnetic wind sensing thermistor elements, for measuring an electrical parameter of the wind sensing thermistor and generating a measurement signal having an amplitude representative of the concentration of the paramagnetic gas in the gas mixture and proportional to the magnitude of the magnetic wind in the presence of the paramagnetic gas.

The magnetic field elements can include first and second magnet elements positioned adjacent each other with a gap between the first and second magnet elements; the magnetic wind generating thermistor elements can include first and second electrically heated magnetic wind generating thermistors positioned opposite each other within the gap; and the magnetic wind sensing thermistor elements can include first and second electrically heated magnetic wind sensing thermistors positioned adjacent the first and second magnetic wind generating thermistors, respectively.

In another aspect of the invention, the signal generating elements comprise a Wheatstone bridge having four branches, the four branches including the first and second magnetic wind generating thermistors and the first and second magnetic wind sensing thermistors. The signal generating elements further comprise temperature control elements for automatically maintaining the first and second magnetic wind generating thermistors and the first and second magnetic wind sensing thermistors at a substantially constant temperature.

In a further aspect of the invention, the signal generating elements comprise a constant temperature electrical bridge and a measurement electrical bridge itself including the Wheatstone bridge. The temperature control elements comprise current control elements, responsive to electrical imbalance between the constant temperature electrical bridge and the measurement bridge, for controlling current to the Wheatstone bridge for maintaining the first and second magnetic wind generating thermistors and the first and second magnetic wind sensing thermistors at a substantially constant temperature.

The signal generating elements can further comprise correction elements responsive to the electrical imbalance between the constant temperature electrical bridge and the measurement electrical bridge, for generating a correction signal, and combining elements for combining the correction signal and the measurement signal to correct the amplitude of the measurement signal responsive to changes in background gases in the gas mixture.

The invention also provides a method for measuring the concentration of a paramagnetic gas in a gas mixture, including the steps of generating an inhomogeneous magnetic field; positioning at least one magnetic wind generating thermistor inside the inhomogeneous magnetic field; positioning at least one magnetic wind sensing thermistor substantially outside the inhomogeneous magnetic field; and electrically heating the magnetic wind generating thermistor to generate a magnetic wind in the presence of a paramagnetic gas, the magnetic wind having a magnitude proportional to concentration of the paramagnetic gas in the gas mixture.

The method further includes measuring an electrical parameter, proportional to temperature, of the magnetic wind sensing thermistor, to sense the magnetic wind generated by the magnetic wind generating thermistor in the presence of a paramagnetic gas; and responding to the electrical parameter of the at least one magnetic wind sensing thermistor to generate a measurement signal having an amplitude representative of the concentration of the paramagnetic gas in the gas mixture and proportional to the magnitude of the magnetic wind in the presence of the paramagnetic gas.

In another aspect of the invention, the magnetic field generating step includes positioning first and second magnet elements adjacent each other with a gap between the first and second magnet elements; the step of positioning at least one magnetic wind generating thermistor includes positioning first and second magnetic wind generating thermistors opposite each other within the gap; and the step of positioning at least one magnetic wind sensing thermistor includes positioning first and second magnetic wind sensing thermistors adjacent the first and second magnetic wind generating thermistors, respectively.

The responding step can include configuring the first and second magnetic wind generating thermistors and the first and second magnetic wind sensing thermistors into a Wheatstone bridge having four branches, and automatically maintaining the first and second magnetic wind generating thermistors and the first and second magnetic wind sensing thermistors at a substantially constant temperature. In a further aspect of the invention, the responding step includes configuring a constant temperature electrical bridge and a measurement electrical bridge, the measurement bridge including the Wheatstone bridge, and the step of automatically maintaining the thermistors at a substantially constant temperature includes responding to electrical imbalance between the constant temperature electrical bridge and the measurement bridge, to control current to the Wheatstone bridge.

The measurement signal can be corrected in response to changes in background gases in the gas mixture, by generating correction signals representative of the electrical imbalance between the constant temperature electrical bridge and the measurement electrical bridge. These correction signals are combined with the measurement signal to compensate for changes in the thermal properties of background gases in the gas mixture.

The invention accordingly comprises the steps and apparatus embodying features of construction, combinations of elements and arrangements of parts adapted to effect such steps, as exemplified in the following detailed disclosure, and the scope of the invention is indicated in the claims.

BRIEF DESCRIPTION OF THE DRAWINGS

For a fuller understanding of the nature and objects of the invention, reference should be made to the following detailed description and the accompanying drawings, in which.

DESCRIPTION OF PREFERRED EMBODIMENTS

Figure 1:
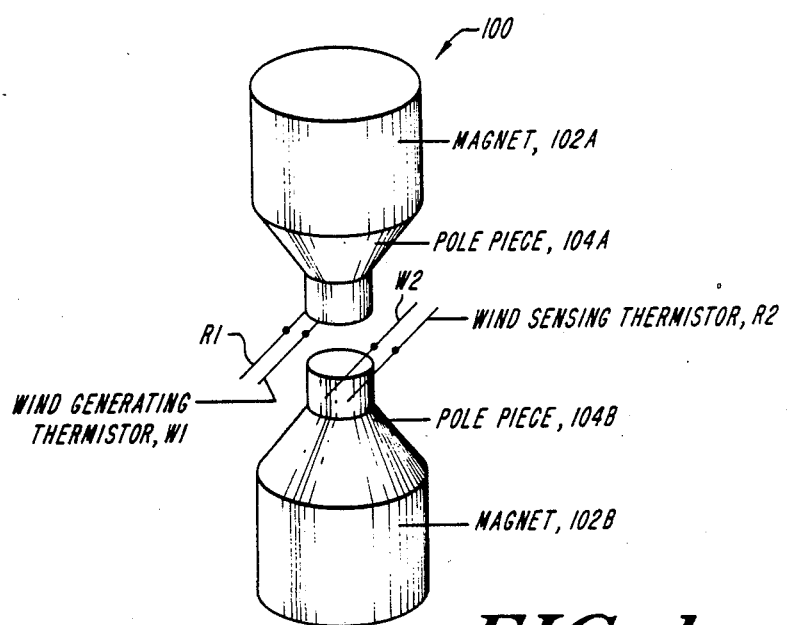
FIG. 1 is a schematic diagram depicting an oxygen sensing cell configured in accordance with the invention.

FIG. 1 is a schematic diagram depicting a configuration of an oxygen sensing cell in accordance with the invention. The oxygen sensor utilizes the "magnetic wind" phenomenon, and includes a sensor cell 100 having two pairs of electrically heated conventional thermistors R1, W1, and R2, W2.

One thermistor of each pair of electrically heated thermistors—i.e. thermistors W1 and W2—is located in a magnetic zone of high field intensity and magnetic field gradient. As illustrated in FIG. 1, this high-intensity, non-uniform magnetic field can be created, for example, by locating thermistors W1 and W2 between the pole pieces 104A and 104B of magnets 102A and 102B, respectively. The second thermistor of each pair of electrically heated thermistors—i.e. thermistors R1 and R2—is located adjacent to W1 and W2, respectively, but substantially outside the region of high magnetic field intensity.

When oxygen is present in the oxygen sensing cell 100, and thermistors W1 and W2 are electrically heated, thermistors W1 and W2, referred to as the "wind generating" thermistors, generate a gas flow in the direction of the adjacent thermistors of each pair located outside the magnetic field—i.e. thermistors R1 and R2. The wind generating thermistors W1 and W2 thus lose heat to the adjacent thermistors R1 and R2 of each pair. Accordingly, the presence of oxygen in the oxygen sensing cell 100 tends to proportionally reduce the temperature of the wind producing thermistors W1 and W2, and tends to increase the temperature of the adjacent thermistors R1 and R2, referred to as "wind sensing" thermistors.

Those skilled in the art will appreciate that the illustrated configuration, utilizing wind generating thermistors W1 and W2 inside the high-intensity magnetic field region created by respective pole pieces 104A and 104B of magnets 102A and 102B, and wind sensing thermistors R1 and R2 outside the high-intensity magnetic field region and adjacent to respective wind generating thermistors W1 and W2, minimizes the position sensitivity of the sensor. As the result of this position insensitivity of the illustrated sensor cell 100, the invention can be advantageously practiced in a portable oxygen sensor. The illustrated arrangement of sensor cell 100 also minimizes the background gas dependency which would otherwise result from variations in thermal conductivity, heat capacity and viscosity. Moreover, the thermistor pairs can be precisely located to maximize signal output.

Figure 2:
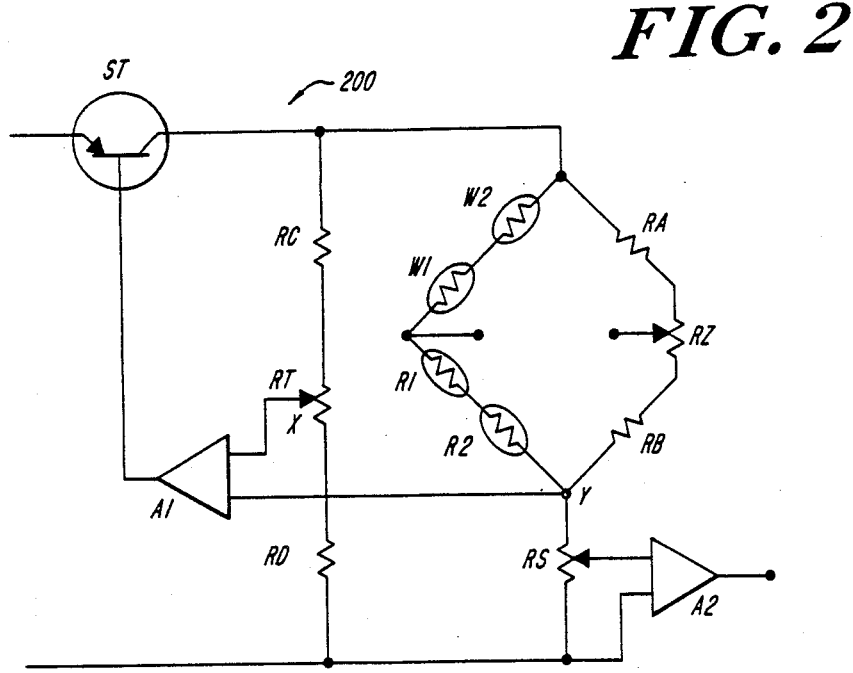
FIG. 2 is a schematic diagram depicting an oxygen sensing circuit in accordance with the invention.

In a preferred embodiment of the invention, the thermistors pairs R1, W1 and R2, W2 are additively connected in a measuring bridge circuit illustrated in FIG. 2. The measuring bridge circuit 200 is unbalanced, due to the resistance change resulting from the thermistor temperature unbalance. This thermistor temperature unbalance, in turn, is proportional to oxygen concentration.

In accordance with the invention, the circuit illustrated in FIG. 2 eliminates the undesirable effects of ambient temperature variations by controlling the temperature of the oxygen sensing elements. The temperature of the oxygen sensing elements is maintained at a substantially constant level by a high precision temperature control loop which includes the illustrated series transistor ST and bridge temperature adjusting element RT. In particular, the illustrated circuit 200 includes a constant temperature bridge, formed by resistors RC, RD, RS, and the oxygen measuring bridge consisting of thermistors W1, W2, R1, R2, RA, and resistances RB and RZ.

Resistors RC, RD, RS, and the oxygen measuring bridge consisting of thermistors W1, W2, R1, R2, RA, and resistances RB and RZ, form the four arms of a Wheatstone bridge. Variable resistor RT is utilized as a bridge temperature adjustment element. Amplifier A1, which can be of conventional design and construction, detects any electrical unbalance between nodes "X" and "Y" and drives the series transistor ST to change the bridge current so as to restore the bridge balance.

This detection and control loop maintains the elements of the oxygen measuring bridge at constant temperature, regardless of any variation in background gas composition that would otherwise affect, through changes in thermal conductivity, the thermistor heat dissipation and temperature. The optimum temperature of the thermistors, in the absence of oxygen, has been found to be approximately 200° C.

An important advantage of the circuit illustrated in FIG. 2 is that the thermistors are maintained at constant temperature. This constant temperature maintains a constant thermal relationship between the thermistor pairs R1, W1, and R2, W2 of the sensing cell 100 illustrated in FIG. 1, thereby minimizing errors in oxygen readings caused by variations in the thermal properties of background gases.

A further advantage of the illustrated configuration is the ability to obtain a signal, at the output of amplifier A2, which can be used as a correction signal, or multiplier, for accurately correcting the oxygen reading obtained from the measuring bridge. This signal is obtained by sensing through RS the current change necessary to restore the bridge balance.

These advantages are best illustrated by way of an example of oxygen measurement utilizing a conventional magnetic wind oxygen sensor. Assume, for example, that a measurement of oxygen is required over a 0% to 5% range, in a gas stream consisting of oxygen, nitrogen, carbon dioxide and hydrogen. In a conventional magnetic wind oxygen analyzer, the measuring bridge is adjusted to yield a zero oxygen reading in 100% nitrogen, and for full scale oxygen reading with 5% oxygen and 95% nitrogen. The conventional magnetic wind oxygen sensor will then provide correct oxygen measurements, within the limits of overall analyzer accuracy, of any oxygen concentration within the measuring range of 0–5% oxygen.

The conventional oxygen analyzer, however, will yield a lower-than-true value when the nitrogen background gas is replaced by hydrogen. In particular, a conventional oxygen sensor may yield a reading as low as 20% of the correct value. The converse problem results when the nitrogen background gas is replaced by carbon dioxide. In this case, a conventional magnetic wind oxygen sensor will yield an oxygen reading as high as twice the correct value.

The above errors, which are typical of prior art magnetic wind oxygen sensors, are due to the large differences in the thermal properties of hydrogen and carbon dioxide in comparison to nitrogen. These differences in thermal properties greatly affect the heat transfer from the wind generating thermistors to the adjacent wind sensing thermistors.

In accordance with the invention, however, the change in the bridge current necessary to compensate for the above variations and to restore the balance between "X" and "Y" is sensed through RS and amplified and scaled by A2, which supplies a correction signal that can be used as a multiplier for the signal supplied by the oxygen measuring bridge. This correction signal is utilized to correct the oxygen measuring bridge signal in units of percent oxygen, regardless of changes in the background gas composition.

It will thus be seen that the invention efficiently attains the objects set forth above, among those made apparent from the preceding description. In particular, the invention provides accurate measurement of oxygen concentration independent of changes in background gas composition. The invention also provides extremely good zero and span stability with low drift, and allows for a compact sensor which can be removed for calibration checks in the laboratory, without breaking electrical or pneumatic connections.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. Apparatus for measuring the concentration of a paramagnetic gas in a gas mixture, comprising magnetic field means for generating an inhomogeneous magnetic field, magnetic wind generating thermistor means, including first and second electrically heated magnetic wind generating thermistors, said first and second magnetic wind generating thermistors having an electrical parameter proportional to temperature, said first and second magnetic wind generating thermistors being positioned inside said inhomogeneous magnetic field, for generating a magnetic wind in the presence of a paramagnetic gas, the magnetic wind having a magnitude proportional to concentration of the paramagnetic gas in the gas mixture, magnetic wind sensing thermistor means, including first and second electrically heated magnetic wind sensing thermistors, said first and second magnetic wind sensing thermistors having an electrical parameter proportional to temperature, said first and second magnetic wind sensing thermistors positioned substantially outside said inhomogeneous magnetic field, for sensing the magnetic wind generated by said first and second magnetic wind generating thermistors in the presence of a paramagnetic gas, and signal generating means, in electrical circuit with said magnetic wind generating thermistor means and said magnetic wind sensing thermistor means, for measuring said electrical parameter of said magnetic wind sensing thermistors and generating a measurement signal having an amplitude representative of the concentration of the paramagnetic gas in the gas mixture and proportional to the magnitude of the magnetic wind in the presence of the paramagnetic gas, said signal generating means including a Wheatstone bridge having four branches, said four branches including said first and second magnetic wind generating thermistors and said first and second magnetic wind sensing thermistors, and temperature control means for automatically maintaining said first and second magnetic wind generating thermistors and said first and second magnetic wind sensing thermistors at a substantially constant temperature.

2. Apparatus according to claim 1, wherein said magnetic field means includes first and second magnet elements positioned adjacent each other with a gap between said first and second magnet elements, said magnetic wind generating thermistor means includes first and second electrically heated magnetic wind generating thermistors positioned opposite each other within said gap, and said magnetic wind sensing thermistor means includes first and second electrically heated magnetic wind sensing thermistors, said first and second magnetic wind sensing thermistors being positioned adjacent said first and second magnetic wind generating thermistors, respectively.

3. Apparatus according to claim 1, wherein said signal generating means includes a constant temperature electrical bridge and a measurement electrical bridge, said measurement bridge including said Wheatstone bridge, and said temperature control means includes current control means, responsive to electrical imbalance between said constant temperature electrical bridge and said measurement bridge, for controlling current to said Wheatstone bridge for maintaining said first and second magnetic wind generating thermistors and said first and second magnetic wind sensing thermistors at a substantially constant temperature.

4. Apparatus according to claim 3, wherein said signal generating means includes correction means responsive to said electrical imbalance between said constant temperature electrical bridge and said measurement electrical bridge, for generating a correction signal, and combining means for combining said correction signal and said measurement signal to correct said amplitude of said measurement signal responsive to changes in background gases in the gas mixture.

5. A method for measuring the concentration of a paramagnetic gas in a gas mixture, comprising the steps of generating an inhomogeneous magnetic field, positioning first and second magnetic wind generating thermistors inside said inhomogeneous magnetic field, positioning first and second magnetic wind sensing thermistors substantially outside said inhomogeneous magnetic field, electrically heating said first and second magnetic wind generating thermistors, to generate a magnetic wind in the presence of a paramagnetic gas, the magnetic wind having a magnitude proportional to concentration of the paramagnetic gas in the gas mixture, measuring an electrical parameter, proportional to temperature, of said first and second magnetic wind sensing thermistors, to sense the magnetic wind generated by said first and second magnetic wind generating thermistors in the presence of a paramagnetic gas, and responding to said electrical parameter of said first and second magnetic wind sensing thermistors to generate a measurement signal having an amplitude representative of the concentration of the paramagnetic gas in the gas mixture and proportional to the magnitude of the magnetic wind int he presence of the paramagnetic gas, said responding step including the steps of configuring said first and second magnetic wind generating thermistors and said first and second magnetic wind sensing thermistors into a Wheatstone bridge having four branches, and automatically maintaining said first and second magnetic wind generating thermistors and said first and second magnetic wind sensing thermistors at a substantially constant temperature.

6. A method according to claim 5, wherein said magnetic field generating step includes the step of positioning first and second magnet elements adjacent each other with a gap between said first and second magnet elements, said step of positioning at least one magnetic wind generating thermistor includes the step of positioning first and second magnetic wind generating thermistors opposite each other within said gap, and said step of positioning at least one magnetic wind sensing thermistor includes the step of positioning first and second magnetic wind sensing thermistors adjacent said first and second magnetic wind generating thermistors, respectively.

7. A method according to claim 5, wherein said responding step includes the step of configuring a constant temperature electrical bridge and a measurement electrical bridge, said measurement bridge including said Wheatstone bridge, and said step of automatically maintaining said thermistors at a substantially constant temperature includes the step of responding to electrical imbalance between said constant temperature electrical bridge and said measurement bridge, to control current to said Wheatstone bridge for maintaining said first and second magnetic wind generating thermistors and said first and second magnetic wind sensing thermistors at a substantially constant temperature.

8. A method according to claim 7, wherein said responding step includes responding to said electrical imbalance between said constant temperature electrical bridge and said measurement electrical bridge to generate a correction signal, and combining said correction signal and said measurement signal to correct said amplitude of said measurement signal responsive to changes in background gases in the gas mixture.

* * * * *